United States Patent [19]

Ohashi et al.

[11] Patent Number: 4,791,198
[45] Date of Patent: Dec. 13, 1988

[54] BETA-LACTAM COMPOUND AND PREPARATION THEREOF

[75] Inventors: Takehisa Ohashi; Kazunori Kan, both of Kobe; Noboru Ueyama; Isao Sada, both of Akashi; Akimasa Miyama, Takasago; Kiyoshi Watanabe, Akashi, all of Japan

[73] Assignee: Kanegafuchi Kagaku Kogyo Kabushiki Kaisha, Osaka, Japan

[21] Appl. No.: 810

[22] Filed: Jan. 6, 1987

Related U.S. Application Data

[63] Continuation-in-part of Ser. No. 750,214, Jul. 1, 1985, abandoned.

[30] Foreign Application Priority Data

Jul. 5, 1984 [JP] Japan ................... 59-139797
Jan. 14, 1986 [JP] Japan ................... 61-5636

[51] Int. Cl.$^4$ ..................... C07D 205/08; C07F 7/18
[52] U.S. Cl. .................................... 540/354; 556/443
[58] Field of Search ........................... 540/354

[56] References Cited

U.S. PATENT DOCUMENTS 4,474,793 10/1984 Ross et al. ................. 540/360

FOREIGN PATENT DOCUMENTS

| | | |
|---|---|---|
| 0070204 | 1/1983 | European Pat. Off. |
| 0078026 | 5/1983 | European Pat. Off. |
| 0106652 | 4/1984 | European Pat. Off. |
| 0167154 | 3/1985 | European Pat. Off. |
| 0167155 | 3/1985 | European Pat. Off. |
| 0181831 | 9/1985 | European Pat. Off. |
| 1770855 | 12/1970 | Fed. Rep. of Germany |
| 2105329 | 3/1983 | United Kingdom ......... 540/310 |
| 2144419 | 3/1985 | United Kingdom |

OTHER PUBLICATIONS

Chiba et al, Chemistry Letters, pp. 1927–1930, 1984.
Yoshida et al, 2-(Alkylthio)penem-3-carboxylic Acids, IV,[1] Synthesis of (Hydroxyethyl)-azetidinone Precursors to 1-Thia Analogs of Thienamycin[2]), Chem. Pharm. Bull., vol 29, pp. 2899–2909, 1981.
Shiozaki et al, Stereocontrolled Syntheses of Chiral and Racemic Key Intermediates to Thienamycin from D-Allo-Threonine and Trans-Crotonic Acid[1], Tetrahedron, vol. 39, pp. 2399–2407, 1983.
Reider et al, Total Synthesis of Thienamycin: A New Approach from Aspartic Acid, Tetrahedron Letters, vol. 23, pp. 2293–2296, 1982.
Notiz uber eine verbesserte Methode zur spezifischen Freisetzung oder Acylierung primarer Hydroxylgruppen ausgedend von pertrimethylsilylierten Polyolen, *Chem Ber*, vol. 107, pp. 721–724, 1974.
Wetter et al, Tetrahedron Letters, vol. 26, No. 45, 1985, pp. 5515–5518.

*Primary Examiner*—Mark L. Berch
*Attorney, Agent, or Firm*—Armstrong, Nikaido, Marmelstein & Kubovcik

[57] ABSTRACT

The present invention relates to β-lactam compound having the formula (I):

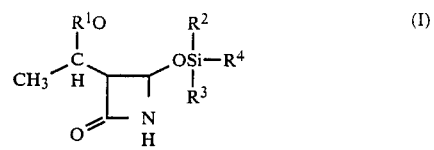

wherein $R^1$ is a trialkylsilyl group, dimethyl-1,1,2-trimethylpropylsilyl group, acetyl group, benzyloxycarbonyl group, O-nitrobenzyloxycarbonyl group, p-nitrobenzyloxycarbonyl group or t-butyl group, $R^2$, $R^3$ and $R^4$ are a member selected from the group consisting of a lower alkyl group having 1 to 6 carbon atoms, phenyl group and an aralkyl group and a process for preparing the compound which comprises reacting enolsilylethers having the formula (III):

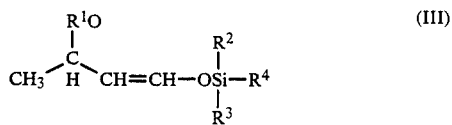

wherein $R^1$, $R^2$, $R^3$ and $R^4$ are as above, with chlorosulfonylisocyanate and then reducing the obtained product. The β-lactam compound of the present invention is a useful intermediate for preparing carbapenem β-lactam compound.

3 Claims, No Drawings

BETA-LACTAM COMPOUND AND PREPARATION THEREOF

CROSS-REFERENCE TO RELATED APPLICATION

This is a continuation-in-part of application Ser. No. 750,214 filed on July 1, 1985, abandoned.

BACKGROUND OF THE INVENTION

The present invention relates to a β-lactam compound having a hydroxyethyl group at the C3-position where the hydroxyl group is protected and having a silylether group at the C4-position, and a process for preparing the compound.

Since the β-lactam compound of the present invention has a highly reactive silylether group, it is a useful intermediate which can be converted into various derivatives. For instance, 3-(1-hydroxyethyl)-4-acetoxyazetidin-2-on and 3-(1-hydroxyethyl)-4-haloazetidin-2-one, which are both useful for preparing thienamycin known as a β-lactam antibiotics of the fourth generation, can be obtained by substitution reaction of the silylether group at the C4-position of the compound of the present invention.

There hitherto has been unknown the β-lactam compound with a silylether group at the C4-postion. Also, there has been unknown a process for preparing the β-lactam compound having an O-protected hydroxyethyl group at the C3-position and a silylether group at the C4-position.

As a result of continuous efforts of the inventors, it has been found that the above β-lactam compound can be a useful intermediate for preparing carbapenem β-lactam compound and the desired β-lactam ring could be formed by a reaction of an enolsilylether and chlorosulfonylisocyanate. Thus, the present invention has been accomplished.

SUMMARY OF THE INVENTION

According to the present invention, there can be provided the β-lactam compound having the formula (I):

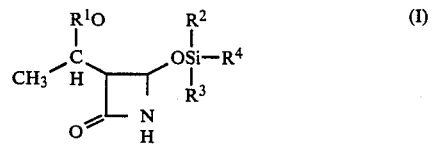

wherein $R^1$ is a protective group for the hydroxyl group, $R^2$ $R^3$ and $R^4$ are a member selected from the group consisting of a lower alkyl group having 1 to 6 carbon atoms, phenyl group and an aralkyl group, and a process for preparation thereof by reacting enolsilylethers having the formula (III):

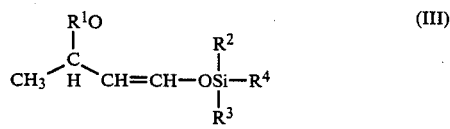

wherein $R^1$, $R^2$, $R^3$ and $R^4$ are as above, with chlorosulfonylisocyanate, followed by reduction.

DETAILED DESCRIPTION

In the above-mentioned formula (I), $R^1$ is a trialkylsilyl group of the formula (II):

wherein each of $R^5$, $R^6$ and $R^7$ is independently a lower alkyl group such as tert-butyldimethylsilyl group, triisopropylsilyl group, isopropyldimethylsilyl group, or dimethyl-1,1,2-trimethylpropylsilyl group, benzyloxycarbonyl group, o-nitrobenzyloxycarbonyl group, p-nitrobenzyloxycarbonyl group or t-butyl group. Among them, trialkylsilyl groups such as tert-butyldimethylsilyl group and triisopropylsilyl group are preferable since the trialkylsilyl groups are stable in preparing the β-lactam compound having the formula (I) and can be removed in an easier manner after obtaining the β-lactam compound, and whereby the desired β-lactam compound can be stereoselectively obtained at high yield.

$R^2$, $R^3$ and $R^4$ in the formula (I) are a member selected from the group consisting of a lower alkyl group having 1 to 6 carbon atoms such as methyl group, isopropyl group, tert-butyl group or 1,1,2-trimethylpropyl group, phenyl group and benzyl group, and $R^2$, $R^3$ and $R^4$ may be the same or different with each other. It is preferred that all of $R^2$, $R^3$ and $R^4$ are methyl group, or both $R^2$ and $R^3$ are methyl group and $R^4$ is t-butyl group, or both $R^2$ and $R^3$ are phenyl group and $R^4$ is t-butyl group or 1,1,2-trimethylpropyl group since, when such substituent groups are employed, the configuration at the C3-position and C4-position on the β-lactam compound become the desirable trans-form and the configuration at the C3-position on the β-lactam ring is apt to become the desirable (R)-form.

With respect to a stereochemistry of the β-lactam compound having the formula (I), three asymmetric carbon atoms are present and thus eight kinds of stereoisomers can be produced. Especially, there is preferred a compound wherein the configuration is (R) at the C3-position, (R) at the C4-position, and (R) at the asymmetric carbon atom on the O-protected hydroxyethyl group.

The usefulness of the β-lactam compound having a silylether group at the C4-position is obvious since, as shown in Reference Example 1, the β-lactam can be converted into a useful intermediate, 3(R)-(1-hydroxyethyl)-4(R)-acetoxyazetidin-2-one.

The process of the present invention is illustrated in the following scheme:

Scheme I

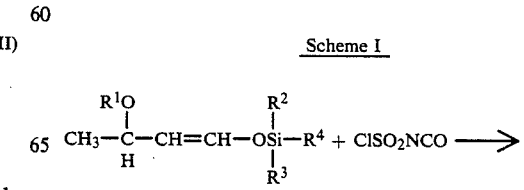

-continued
Scheme I

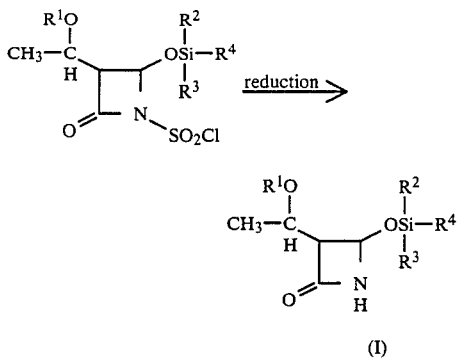

(I)

Wherein $R^1$, $R^2$ $R^3$ and $R^4$ are as above.

Examples of the enolsilyl ether employed as a starting material in the present invention are, for instance, 3-tert-butyldimethylsilyloxybute-1-nyl trimethylsilyl ether, 3-tert-butyldimethylsilyloxybute-1-nyl dimethylisobutylsilyl ether, 3-tert-butyldimethylsilyloxybute-1-nyl-tert-butyldimethylsilyl ether, 3-tert-butyldimethylsilyloxybute-1-nyl-tert-butylmethylphenylsilyl ether, 3-tert-butyldimethylsilyloxybute-1-nyl-tert-butyldiphenylsilyl ether, 3-tert-butyldimethylsilyloxybute-1-nyl-dimethyl-1,1,2-trimethylpropylsilyl ether, 3-triisopropylsilyloxybute-1-nyl trimethylsilyl ether, 3-triisopropylsilyloxybute-1-nyl-tert-butyldimethylsilyl ether, 3-isopropyldimethylsilyloxybute-1-nyl-trimethylsilyl ether, 3-dimethyl-1,1,2-trimethylpropylsilyloxybute-1-nyl-trimethylsilyl ether, 3-dimethyl-1,1,2-trimethylpropylsilyloxybute-1-nyl-dimethylisobutylsilyl ether, 3-dimethyl-1,1,2-trimethylpropylsilyloxybute-1-nyl-tert-butyldimethylsilyl ether, 3-dimethyl-1,1,2-trimethylpropyl-silyloxybute-1-nyl-tert-butylmethylphenylsilyl ether, 3-dimethyl-1,1,2-trimethylpropylsilyloxybute-1-nyl-tert-butyldiphenylsilyl ether, 3-dimethyl-1,1,2-trimethylpropylsilyloxybute-1-nyl-dimethyl-1,1,2-trimethylpropylsilyl ether, 3-isopropyldimethylsilyloxybute-1-nyl-trimethylsilyl ether, 3-acetoxybute-1-nyl-trimethylsilyl ether, 3-acetoxybute-1-nyl-tert-butyldimethylsilyl ether, 3-acetoxybute-1-nyl-tert-butyldiphenylsilyl ether, 3-tert-butoxybute-1-nyl-trimethylsilyl ether, 3-tert-butoxybute-1-nyl-tert-butyldimethylsilyl ether, 3-tert-butoxybute-1-nyl-tert-butyldiphenylsilyl ether, 3-benzyloxycarbonyloxybute-1-nyl trimethylsilyl ether, 3-benzyloxycarbonyloxybute-1-nyl-tert-butyldimethylsilyl ether, 3-benzyloxycarbonyloxybute-1-nyl-tert-butyldiphenyl ether, 3-p-nitrobenzyloxycarbonyloxybute-1-nyl trimethylsilyl ether, 3-p-nitrobenzyloxycarbonyloxybute-1-nyl-tert-butyldimethylsilyl ether, 3-p-nitrobenzyloxycarbonyloxybute-1-nyl-tert-butyldiphenylsilyl ether, 3-o-nitrobenzyloxycarbonyloxybute-1-nyl-trimethylsilyl ether, 3-o-nitrobenzyloxycarbonyloxybute-1-nyl-tert-butyldimethylsilyl ether, 3-o-nitrobenzyloxycarbonyloxybute-1-nyl-tert-butyldiphenylsilyl ether and the like, preferably, enolsilyl ether having the formula (III) wherein $R^1$ is a tert-butyldimethylsilyl group such as 3-tert-butyldimethylsilyloxybute-1-nyl trimethylsilyl ether, 3-tert-butyldimethylsilyoxybute-1-nyl-tert-butyldimethylsilyl ether, 3-tert-butyldimethylsilyloxybute-1-nyl-tert-butyldiphenylsilyl ether, 3-tert-butyldimethylsilyloxybute-1-nyl-tert-butylmethylphenylsilyl ether or 3-tert-butyldimethylsilyloxy-bute-1-nyl dimethylisobutylsilyl ether. These materials can be prepared by the following scheme starting from 3-hydroxybutyric acid ester:

Scheme II

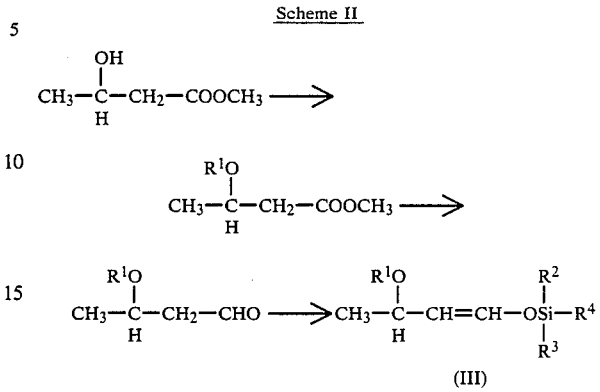

(III)

The configuration of O-protected hydroxyethyl group at the C3-position of the β-lactam compound (I) of the present invention is preferably (R). To obtain such a β-lactam compound, the reaction of scheme II is conducted by employing an optically active enolsilylether which is obtained from optically active 3(R)-hydroxybutyric acid ester.

In the reaction of the enolsilylether with chlorosulfonylisocyanate to form the β-lactam ring, the configuration of the resulting β-lactam compound varies depending on the kind of the silylether group. Examples of the preferable silylether groups for obtaining the β-lactam compound (I) of the C3(R), C4(R) configuration which is suitable for synthesis of carbapenem β-lactam antibiotics such as thienamycin are, for instance, trimethylsilyl group, tert-butyldiphenylsilyl group, tert-butyldimethylsilyl group, tert-butylmethylphenylsilyl group and dimethylisobutylsilyl group. Protective group $R^1$ for hydroxyl group of the enolsilylether is preferably tert-butyldimethylsilyl group or dimethyl-1,1,2-trimethylpropylsilyl group from the viewpoint of stereochemistry as mentioned above and good reactivity with chlorosulfonylisocyanate. The reaction of enolsilylether with chlorosulfonylisocyanate can be conducted either without any solvent or in the presence of an organic solvent which does not react with both chlorosulfonylisocyanate and enolsilylethers, e.g. methylene chloride, toluene, tetrahydrofuran, n-hexane and ethylether. The reaction temperature is from −70° C. to around room temperature. Preferably, the reaction is carried out at a temperature of −50° C. to 0° C., while controlling heat generation for instance, by adding dropwise chlorosulfonylisocyanate to an enolsilylether solution. The enolsilylether solution may be added dropwise to chlorosulfonylisocyanate or solution containing chlorosulfonylisocyanate. The enolsilylether and chlorosulfonylisocyanate are used in such an amount that the molar ratio of these materials is around 1:1. The reaction time is selected from ten minutes to several hours.

The obtained β-lactam compound can be converted into the desired β-lactam compound by reducing the N-sulfonyl chloride group. Examples of the reducing agent used in the above reduction are, for instance, a metal hydride such as lithium aluminum hydride, sodium boron hydride or sodium bis(2-methoxyethoxy)aluminum hydride, Raney nickel and the like. A thiol compound such as thiophenol or alkylmercaptan can also be used as a reducing agent. When a metal hydride such as lithium aluminum hydride or sodium bis(2-methoxyethoxy)aluminum hydride is employed as the reducing agent, the reduction is carried out in an organic solvent such as tetrahydrofuran, toluene or ethylether. When a thiol compound is employed as the reducing agent, the reduction is carried out in the above organic solvent in which a base such as pyridine is coexistent. The reaction temperature of the reduction is in the range from $-40°$ C. to $0°$ C. Among the above reducing agents, lithium aluminum hydride or sodium bis(2-methoxyethoxy)aluminum hydride is preferable.

After the reduction is completed, water is added to the reaction system. The desired β-lactam compound is extracted with an organic solvent such as ethylether, toluene or ethylacetate and dried with a dehydrating agent such as magnesium sulfate. The solvent is distilled away under reduced pressure to give the β-lactam compound having an O-protected hydroxyethyl group at the C3-position and a silylether group at the C4-position. If necessary, the thus obtained β-lactam compound can be isolated and purified by column chromatography.

The present invention is more particularly explained by the following Examples and Reference Examples. However, it is to be understood that the present invention is not limited to these Examples and various changes and modifications can be made without departing from the scope and spirit of the present invention.

EXAMPLE 1

[Preparation of (3R,4R,5R)-3-(1-tert-buthyldimethylsilyloxyethyl)-4-trimethylsilyloxyazetidin-2-one]

One gram of (3R)-3-tert-butyldimethylsilyloxybute-1-nyl trimethylsilyl ether (a mixture of the transform and the cis-form in a ratio of 9:1) was added to 5 ml of ether, and thereto 0.3 ml of chlorosulfonylisocyanate was added over 20 minutes with stirring and cooling to $-50°$ C. under nitrogen gas. The reaction mixture was slowly warmed to $-40°$ C. and stirred further for 30 minutes. Then the reaction mixture was again cooled to $-60°$ C., and thereto 0.08 g of LiAlH$_4$ was added. The resulting mixture was slowly warmed to $-40°$ C. and stirred for 60 minutes. The resulting mixture was then quickly added to a mixed solution of 150 ml of ice water and 100 ml of ether and stirred for 30 minutes. After completion of the stirring, the insoluble portion was removed by Hyflo Super-Cel. The ether layer was washed with saturated solution of salt and dried with magnesium sulfate. Then ether was distilled away under reduced pressure to give 0.6 g of a liquid of the desired β-lactam as a mixture of (3R,4R,5R)-form and (3S,4S,5R)-form (10:1). The obtained β-lactam was purified by means of silica-gel column chromatography (hexane:methylene chloride=50:1) and a portion which predominantly contained (3R,4R,5R)-form was collected and concentrated to give 0.3 g of the desired product as a semisolid.

The obtained β-lactam had the following properties.
(3R,4R,5R)-form
$[\alpha]_D^{25} = -12.4°$ C. (C=1, CCl$_4$)
$^1$HNMR (90 MHz, CCl$_4$) δ(ppm): 0.08 (6H, S), 0.18 (9H, S), 0.88 (9H, S), 1.25 (3H, d), 2.97 (1H, dd), 4.17 (1H, m), 5.37 (1H, d) and 6.60 (1H, broad)

EXAMPLE 2

[Preparation of (3R,4R,5R)-3-(1-tert-buthyldimethylsilyloxyethyl)-4-tert-butyldimethylsilyloxyazetidin-2-one]

One gram of (3R)-3-tert-butyldimethylsilyloxybute-1-nyl tert-butyldimethylsilyl ether (a mixture of the trans-form and the cis-form in a ratio of 3:2) was added to 8 ml of ether, the mixture was cooled to $-50°$ C. under nitrogen gas and thereto 0.25 ml of chlorosufonylisocyanate was added over 10 minutes with stirring and cooling to $-50°$ C. under nitrogen gas. The reaction mixture was slowly warmed to $-20°$ C. and stirred for 20 minutes. Then the reaction mixture was again cooled to $-60°$ C. and thereto 0.066 g of LiAlH$_4$ was added. The resulting mixture was again slowly warmed to $-40°$ C. and stirred for 60 minutes. The resulting mixture was then quickly poured into a mixed solution of 100 ml of ice water and 100 ml of ether and the mixture was stirred for 30 minutes. After completion of the stirring, the separated ether layer was successively washed with 5% aqueous soluton of NaHCO$_3$, an aqueous solution of hydrochloric acid of pH3 and saturated solution of salt and dried with magnesium sulfate. The solvent was distilled away to give 0.9 g of the desired β-lactam as a mixture of (3R,5R)-form and (3S,5R)-form, whose ratio was 3:2.

The obtained β-lactam was purified by means of silica-gel column chromatography (hexane:ethyl acetate=10:1) to give 0.25 g of the desired (3R,4R,5R) β-lactam and 0.13 g of (3S,4S,5R) β-lactam as a solid.

Each β-lactam had the following properties.
(3R,4R,5R)-form
$[\alpha]_D^{25} = -8.3°$. (C=1, CCl$_4$)
$^1$HNMR (90 MHz, CDCl$_3$) δ(ppm): 0.08 (CH$_3$×2, s), 0.13 (CH$_3$×2, s), 0.90 (9H, s), 0.93 (9H, s), 1.27 (CH$_3$, d), 2.95 (1H, dd), 4.13 (1H, m), 5.37 (1H, d) and 6.13 (NH, broad)
mp: 131° to 133° C.
(3S,4S,5R)-form
$[\alpha]_D^{25} = -33.1°$ (C=1, CCl$_4$)
$^1$HNMR (90 MHz, CDCl$_3$) δ(ppm): 0.10 (CH$_3$×2, s), 0.13 (CH$_3$×2, s) 0.08 (9H, s), 0.90 (9H, s), 1.31 (CH$_3$, d), 3.05 (1H, dd), 4.22 (1H, m), 5.27 (1H, d) and 6.37 (1H, broad)
mp: 43° to 45° C.

EXAMPLE 3

[Preparation of (3R,4R,5R)-3-(1-tert-butyldimethylsilyloxyethyl)-4-tert-butyldimethylsilyloxyazetidin-2-one]

One gram of (3R)-3-tert butyldimethylsilyloxybute-1-nyl-tert-butyldimethylsilyl ether (a mixture of the trans-form and the cis-form in a ratio of 3:2) was added to 8 ml of hexane, and thereto 0.25 ml of chlorosulfonylisocyanate was added over 10 minutes with stirring and cooling to $-50°$ C. under nitrogen gas. The reaction mixture was slowly warmed to $-20°$ C. and stirred for 20 minutes. Then the reaction mixture was again cooled to $-60°$ C. and thereto a solution of 0.7 g of thiophenol in 2 ml of hexane was added. After the solution was stirred for 10 minutes, a solution of 0.4 g of pyridine in 2 ml of hexane was further added thereto. The mixture was slowly warmed to room temperature with stirring, and thereto 50 ml of hexane was added. Then the resulting mixture was successively washed with 5% aqueous solution of NaHCO$_3$, an aqueous solution hydrochloric acid of pH 3 and saturated solution of salt and dried with magnesium sulfate. Hexane was distilled away under reduced pressure to give 0.7 g of the desired β-lactam as a mixture of (3R,4R,5R)-form and (3S,4S, 5R)-form, whose ratio was 3:2.

The obtained β-lactam was separated and purified by means of silica-gel column chromatography (hexane:ethyl acetate=10:1) to give 0.18 g of (3R,4R,5R) β-lactam and 0.10 g of (3S,4S,5R) β-lactam.

The properties of each β-lactam were same as those shown in Example 2.

EXAMPLE 4

[Preparation of (3R,4R,5R)-3-(1-tert-butyldimethylsilyloxy)-4-tert-butylmethylphenylsilyloxyazetidin-2-one]

One gram of (3R)-3-tert-butyldimethylsilyloxybute-1-nyl-tert-butylmethylphenylsilyl ether (a mixture of the trans-form and the cis-form in a ratio of 7:1) was added to 5 ml of ether, the mixture was cooled to −50° C. under nitrogen gas and thereto 0.22 ml of chlorosulfonylisocyanate was added over 10 minutes with stirring and cooling to −50° C. under nitrogen gas. The reaction mixture was slowly warmed to −40° C. and stirred further for 30 minutes. Then the reaction mixture was again cooled to −60° C. and thereto 0.06 g of LiAlH$_4$ was added. The mixture was slowly warmed to −45° C. and stirred for 40 minutes. The mixture was then quickly added to a mixture of 150 ml of ice water and 100 ml of ether and stirred for 30 minutes. After completion of the stirring, the obtained mixture was separated and the organic layer was successively washed with 5% aqueous solution of NaHCO$_3$, a hydrochloric acid solution of pH 3 and saturated solution of salt and dried with magnesium sulfate. The solvent was distilled away to give 0.98 g of a crude product as an oil.

The obtained β-lactam had the following properties. (3R,4R,5R)-form

NMR (CDCl$_3$) δ(ppm): 0.00 (6H, s), 0.43 (3H, s), 0.80 (9H, s), 0.90 (9H, s), 1.19 (3H, d), 2.99 (1H, dd), 4.10 (1H, m), 5.35 (1H, d), 6.63 (1H, d) and 7.37 (5H, m)

EXAMPLE 5

[Preparation of (3R,4R,5R)-3-(1-tert-butyldimethylsilyloxy)-4-dimethylisobutylsilyloxyazetidin-2-one]

One gram of (3R)-3-tert-butyldimethylsilyloxybute-1-nyl dimethylisobutylsilyl ether (a mixture of the trans-form and the cis-form in a ratio of 5:1) was added to 6 ml of ether, and thereto 0.26 ml of chlorosulfonyl isocyanate was added over 10 minutes with stirring and cooling to −60° C. under nitrogen gas. The reaction mixture was slowly warmed to −50° C. and stirred for further 30 minutes. Then the reaction mixture was again cooled to −60° C. and thereto 0.066 g of LiAlH$_4$ was added. The mixture was slowly warmed to −50° C. and stirred for 60 minutes. The reaction mixture was quickly added to a mixture of 150 ml of ice-water and 100 ml of ether and the mixture was stirred for 30 minutes. After stirring, the resulting mixture was fractionated, and then the organic layer was washed with a 5% aqueous solution of NaHCO$_3$, a hydrochloric acid solution of pH 3 and then saturated saline solution. After drying the resultant with magnesium sulfate, the solvent was distilled away to give 0.59 g of the crude product as an oily material.

The obtained β-lactam had the following properties. (3R,4R,5R)-form

NMR (CDCl$_3$) δ(ppm): 0.03 (6H, s) 0.15 (6H, s), 0.60 (2H, d), 0.87 (9H, s), 0.93 (6H, d), 1.22 (3H, d), 1.80 (1H, m), 2.85 (1H, dd), 4.15 (1H, m), 5.26 (1H, d) and 7.77 (1H, broad s)

EXAMPLE 6

[Preparation of (3R,4R,5R)-3-(1-tert-butyldimethylsilyloxyethyl)-4-trimethylsilyloxyazetidin-2-one]

One gram of (3R)-3-tert-butyldimethylsilyloxybute-1-nyl trimethylsilyl ether (a mixture of the transform and the cis-form in a ratio of 9:1) was added to 5 ml of ether, and thereto 0.3 ml of chlorosulfonylisocyanate was added dropwise over 20 minutes with stirring and cooling to −50° C. under nitrogen gas. After the mixture was stirred for 90 minutes at −50° C., it was cooled to −70° C. and thereto solution where 178 mg of aluminum chloride and 152 mg of sodium boron hydride were dissolved in 8 ml of diglyme was added. The mixture was slowly warmed to −60° C. and stirred for 1 hour, which was quickly added to an ice-cooled mixture of 0.5M aqueous solution of Rochelle salt and 100 ml of hexane and the mixture was stirred for 20 minutes under cooling with ice. After completion of the stirring, the insoluble portion was filtered with Hyflo Super-Cel and the hexane layer was dried with magnesium sulfate. The solvent was distilled away to give 0.3 g of the desired β-lactam which predominantly contained (3R,4R,5R)-form.

EXAMPLE 7

[Preparation of (3R,4R,5R)-3-(1-tert-butyldimethylsilyloxyethyl)-4-trimethylsilyloxyazetidin-2-one]

One gram of (3R)-3-tert-butyldimethylsilyloxybute-1-nyl trimethylsilyl ether (a mixture of the transform and the cis-form in a ratio of 9:1) was added to 5 ml of toluene, and thereto 0.32 ml of chlorosulfonylisocyanate was added dropwise over 10 minutes with stirring and cooling to −50° C. under nitrogen gas. After the mixture was stirred for 2 hours at −50° C., it was cooled to −70° C., and thereto 11 ml of toluene and then 4 ml of toluene solution containing 1M sodium bis(2-methoxyethoxy)aluminum hydride were added. The mixture was slowly warmed to −50° C. and stirred for 60 minutes. The reaction mixture was quickly added to an ice-cooled mixture of 100 ml of 0.5M aqueous solution of Rochelle salt and 100 ml of toluene and the mixture was stirred for 30 minutes under cooling with ice. After completion of the stirring, the insoluble portion was filtered with Hyflo Super-Cel, and the toluene layer was washed with saturated solution of salt and dried with magnesium sulfate. Toluene was distilled away under reduced pressure to give 0.81 g of white crystal of the desired β-lactam containing (3R,4R,5R)-form and (3S,4S,5R)-form in a ratio of 10:1.

EXAMPLE 8

[Preparation of (3R,4R,5R)-3-(1-isopropyldimethylsilyloxyethyl)-4-trimethylsilyloxyazetidin-2-one]

One gram of (3R)-3-isopropyldimethylsilyloxybute-1-nyl trimethylsilyl ether (a mixture of the transform and the cis-form in a ratio of 8:1) was added to 5 ml of ether, and thereto 0.3 ml of chlorosulfonylisocyanate was added dropwise over 25 minutes with stirring and cooling to −60° C. under nitrogen gas. After the mixture was stirred for 2 hours at −60° C., it was cooled to −70° C., and thereto 10 ml of toluene and then 4 ml of toluene solution containing 1M sodium bis(2-methoxyethoxy)aluminum hydride were added. The mixture was slowly warmed to −50° C. and stirred for 60 minutes. The reaction minture was quickly added to an ice cooled mixture of 50 ml of 0.5M aqueous solution of Rochell salt and 50 ml of toluene and the resulting mixture was stirred for 30 minutes with cooling by ice. After completion of the stirring, the insoluble portion was filtered with Hyflo Super-Cel and the toluene was washed with saturated solution of salt and dried with magnesium sulfate. Toluene was distilled away under reduced pressure to give 0.61 g of the desired β-lactam which predominantly contained (3R,4R,5R)-form as an oil.

The obtained β-lactam had the following properties.
(3R,4R,5R)-form
$^1$HNMR (90 MHz, CCl$_4$) δ(ppm): 0.07 (6H, s), 0.92 (7H), 1.21 (3H, d), 2.85 (1H, dd) 4.05 (1H, m), 5.21 (1H, d) and 7.31 (NH)

EXAMPLE 9

[Preparation of (3R,4R,5R)-3-[1-(dimethyl-1,1,2-trimethylpropylsilyloxy)ethyl]-4-trimethylsilyloxyazetidin-2-one]

Two grams of (3R)-3-(dimethyl-1,1,2-trimethylpropylsilyloxy)bute-1-nyl trimethylsilyl ether (a mixture of the trans-form and the cis-form in a ratio of 9:1) was added to 10 ml of toluene, and thereto 0.64 ml of chlorosulfonylisocyanate was added over 20 minutes with stirring and cooling to −50° C. under nitrogen gas. After the mixture was reacted for 1 hour at −50° C., a solution of 1.6 g of NaAlH$_2$(OCH$_2$CH$_2$OCH$_3$)$_2$ dissolved in 10 ml of toluene was added thereto for 10 minutes at −55° C. Then, after stirring for 60 minutes, the reaction mixture was added to 50 ml of water and adjusted to pH 3 with sulfuric acid. The organic layer was separated and dried with magnesium sulfate. Then toluene was distilled away under reduced pressure to give 1.73 g of a semisolid of the desired β-lactam containing (3R,4R,5R)-form and (3S,4S,5R)-form in a ratio of 10:1.

The obtained β-lactam had the following properties.
(3R,4R,5R)-form
$^1$HNMR (90 MHz, CDCl$_3$) δ(ppm): 0.02 (6H, s), 0.08 (9H, s), 0.72 (6H, s), 0.75 (6H, d), 1.12 (3H, d), 1.5 (1H, m), 2.85 (1H, dd), 4.08 (1H, m), 5.28 (1H, d), 6.45 (NH, broad)

EXAMPLE 10

[Preparation of (3R,4R,5R)-3-[1-dimethyl-1,1,2-trimethylpropylsilyloxy)ethyl]-4-tert-butyldimethylsilyloxyazetidin-2-one]

Two grams of (3R)-3-(dimethyl-1,1,2-trimethylpropylsilyloxy)-bute-1-nyl-tert-butyldimethylsilyl ether (a mixture of the trans-form and the cis-form in a ratio of 3:2) was added to 10 ml of toluene and thereto 0.79 ml of chlorosulfonylisocyanate was added for 20 minutes with stirring and cooling to −50° C. under nitrogen gas. After the mixture was reacted for 1 hour at −50° C., a solution of 1.97 g of NaAlH$_2$(OCH$_2$CH$_2$OCH$_3$)$_2$ dissolved in 10 ml of toluene was added thereto for 10 minutes at −55° C. Then, after stirring for 60 minutes, the reaction mixture was added to 50 ml of water and adjusted to pH 3 with sulfuric acid. The organic layer was separated and dried with magnesium sulfate. Then toluene was distilled away under reduced pressure to give 2.13 g of a semi-solid of the desired β-lactam containing (3R,4R,5R)-form and (3S,4S,5R)-form in a ratio of 3:2. The obtained β-lactam had the following properties.

(3R,4R,5R)-form
$^1$HNMR (90 MHz, CDCl$_3$) δ(ppm): 0.02 (6H, s), 0.08 (6H, s), 0.72 (6H, s), 0.75 (6H, d), 0.90 (9H, s), 1.13 (3H, d), 1.5 (1H, m), 2.87 (1H, dd), 4.10 (1H, m), 5.30 (1H, d), 6.50 (NH, broad)

EXAMPLE 11

[Preparation of (3R,4R,5R)-3-[1-(dimethyl-1,1,2-trimethylpropylsilyloxy)ethyl]-4-dimethylsopropylsilyloxy-azetidin-2-one]

Two grams of (3R)-3-(dimethyl-1,1,2-trimethylpropylsilyloxy)-bute-1-nyl-dimethylisopropylsilyl ether (a mixture of the trans-form and the cis-form in a ratio of 5:1) was added to 10 ml of toluene and thereto 0.7 ml of chlorosulfonylisocyanate was added over 20 minutes with stirring and cooling to −50° C. under nitrogen gas. After the mixture was reacted for 1 hour at −50° C., a solution of 2.15 g of NaAlH$_2$(OCH$_2$CH$_2$OCH$_3$)$_2$ dissolved in 10 ml of toluene was added thereto over 10 minutes at −55° C. Then, after stirring for 60 minutes, the reaction mixture was added to 50 ml of water and adjusted to pH 3 with sulfuric acid. The organic layer was separated and dried with magnesium sulfate. Then toluene was distilled away under reuced pressure to give 1.95 g of a crude product as an oil. The obtained β-lactam had the following properties.

(3R,4R,5R)-form
$^1$HNMR (90 MHz, CDCl$_3$) δ(ppm): 0.02 (6H, s), 0.07 (6H, s), 0.72 (6H, s), 0.75 (6H, d), 0.91 (7H), 1.12 (3H, d), 1.51 (1H, m), 2.85 (1H, dd), 4.07 (1H, m), 5.27 (1H, d), 6.46 (NH, broad)

REFERENCE EXAMPLE 1

[Preparation of (3R,4R)-4-acetoxy-3-[(R)-1-tert-butyldimethylsilyloxyethyl]-azetidin-2-one]

One gram of (3R,5R)-3-(1-tert-butyldimethylsilyloxyethyl)-4-trimethylsilyloxyazetidin-2-one was dissolved in 10 ml of DMF (dimethilformamide) thereto 0.89 g of triethylamine and 0.61 g of tert-butyldimethylsilyl chloride were added and the mixture was stirred for 9 hours at room temperature. After completion of the reaction, DMF was distilled away under reduced pressure and thereto 30 ml of hexane was added. The solution was successively washed with 2.5% aqueous solution of NaHCO$_3$, aqueous solution of hydrochloric acid of pH 3 and saturated solution of salt and dried with magnesium sulfate. The solvent was distilled away to give 1.24 g of liquid crude product. There was added 1.0 g of the obtained liquid to 5 ml of methylene chloride, and thereto 0.85 g of dimethylaminopyridine and 1.1 ml of acetic anhydride were further added and the mixture was reacted for 6 hours at room temperature. After the solution was washed successively with 5% aqueous solution of NaHCO$_3$, aqueous solution of hydrochloric acid of pH 3 and saturated solution of salt and dried with magnesium sulfate, the solvent was distilled away to give 0.8 g of liquid of a crude product, which was purified by silica-gel column chromatography (benzene:hexane=2:1) to give 0.5 g of (3R,4R,5R)-4-acetoxy-1-(tert-buthyldimethylsilyl)-3-(1-tert-butyldimethylsilyloxyethyl)-azetidin-2-one as a liquid. There was added 0.5 g of the obtained liquid to 2 ml of THF (tetrahydrofuran), and thereto 2 ml of THF in which 0.4 g of tetrabutylammonium fluoride and 0.17 g of acetic acid were dissolved were added. The mixture was stirred for 30 minutes at room temperature, thereto 20 ml of ethyl acetate was added and the mixture was successively washed with 5% aqueous solution of NaHCO$_3$ and saturated solution of salt, dried with magnesium sulfate and the solvent was distilled away to give 0.30 g of crystal of the desired product. The obtained crystal was purified by means of silica-gel column chromatography (benzene:ethyl acetate=6:1) to give 0.27 g of the desired β-lactam as a solid.

The obtained β-lactam had the following properties.
mp: 107° to 108° C.
$[\alpha]_D^{25} = +50°$ (C=0.5, CHCl$_3$)
$^1$HNMR (90MH$_2$, CDCl$_3$) δ(ppm): 0.08 (6H, s), 0.84 (9H, s), 1.20 (3H, d), 2.01 (3H, s), 3.04 (1H, dd), 4.12 (1H, m), 5.76 (1H, d) and 6.73 (NH)

REFERENCE EXAMPLE 2

[Preparation of (3R)-3-tert-butyldimethylsilyloxybute-1-nyl trimethylsilyl ether]

There was added 8.0 g of (3R)-3-tert-butyldimethylsilyloxybutylaldehyde to 40 ml of methylene chloride, 8.0 g of triethylamine and 12 ml of trimethylsilyl chloride were added to the above solution and the mixture was refluxed for 13 hours. After completion of the reaction, the solvent was distilled away and thereto n-hexane was added. The resultant was successively washed with 5% aqueous solution of NaHCO$_3$, aqueous solution of hydrochloric acid of pH 3 and saturated solution of salt, dried with magnesium sulfate and the solvent was distilled away to give 10 g of a liquid. The obtained liquid was distilled under reduced pressure to give 8.0 g of the desired product (bp 85° C./3 mmHg). The obtained product was a mixture of the trans-form and the cis-form in a ratio of 15:1.

The obtained β-lactam had the following properties.
$[\alpha]_D^{25} = -3.2°$ (C=1, CCl$_4$)
$^1$HNMR (90 MHz, CCl$_4$) (Trans-form) δ(ppm): 0.11 (6H, s), 0.25 (9H, s), 0.90 (9H, s), 1.25 (3H, d), 4.25 (b 1H, m), 4.95 (1H, dd) and 6.28 (1H, d)

REFERENCE EXAMPLE 3

[Preparation of (3R)-3-tert-butyldimethylsilyloxybute-1-nyl-tert-butyldimethylsilyl ether]

There was added 8.0 g of (3R)-3-tert-butyldimethylsilyloxybutylaldehyde to 50 ml of DMF, to which 12.0 g of tert-butyldimethylsilyl chloride and 16.0 g of triethylamine were added and the mixture was stirred for 13 hours at 90° C. After completion of the reaction, DMF was distilled away under reduced pressure and thereto 100 ml of n-hexane was added, which was successively washed with 5% aqueous solution of NaHCO$_3$, an aqueous solution of hydrochloric acid of pH 3 and saturated solution of salt, dried with magnesium sulfate and the solvent was distilled away to give 8.0 g of a liquid. The obtained liquid was distilled away under reduced pressure to give 5.0 g of the desired product (bp 65° C./1 mmHg). The obtained product was a mixture of the trans-form and the cis-form in a ratio of 3:2.

The obtained β-lactam had the following properties.
$[\alpha]_D^{25} = -14.96°$ (C=2, CCl$_4$)
$^1$HNMR (90 MHz, CCl$_4$) δ(ppm):
Trans-form 0.07 (6H, s), 0.17 (6H, s), 0.90 (9H, s), 0.97 (9H, s), 1.20 (3H, d), 4.20 (1H, m), 4.95 (1H, dd) and 6.26 (1H, d)
Cis-form 0.07 (6H, s), 0.17 (6H, s), 0.90 (9H, s), 0.97 (9H, s), 1.15 (3H, d), 4.20 (1H, m), 4.48 (1H, dd) and 5.97 (1H, d)

REFERENCE EXAMPLE 4

[Preparation of (3R)-3-tert-butyldimethylsilyloxybute-1-nyl-tert-butylmethylphenylsilyl ether]

There was added 10.0 g of (3R)-3-tert-butyldimethylsilyloxybutylaldehyde to 40 ml of DMF. To this solution 6.6 of dimethylaminopyridine and 10.4 g of tert-butylmethylphenylsilyl chloride were added and the mixture was stirred for 14 hours at 75° C. After completion of the reaction, DMF was distilled away under reduced pressure and thereto 100 ml of n-hexane was added, which was successively washed with 5% aqueous solution of NaHCO$_3$, an aqueous solution of hydrochloric acid of pH 3 and saturated solution of salt, dried with magnesium sulfate and the solvent was distilled away to give 10.2 g of liquid. The obtained liquid was purified by means of silica-gel column chromatography (hexane:ethyl acetate=20:1) to give 7.2 g of the desired product. The obtained product was a mixture of the trans-form and the cis-form in a ratio of 7:1.

The obtained β-lactam had the following properties.
$[\alpha]_D^{25} = -5.3°$ (C=1, CCl$_4$)
$^1$HNMR (90 MHz, CDCl$_3$) δ(ppm):
Trans-form 0.00 (6H, s), 0.40 (3L H, s), 0.85 (9H, s), 0.93 (9H, s), 1.18 (3H, d), 4.20 (1H, m), 5.06 (1H, dd), 6.35 (1H, d) and 7.40 (5H, m)

REFERENCE EXAMPLE 5

[Preparation of (3R)-3-tert-butyldimethylsilyloxybute-1-nyl dimethylisobutylsilyl ether]

There was added 20.0 g of (3R)-3-tert-butyldimethylsilyloxybutylaldehyde to 80.0 ml of DMF, 16.3 ml of TMEDA (tetramethylenediamine) and 14.8 g of isobutyldimethylsilyl chloride were added to the above solution and the mixture was stirred for 3 hours at 80° C. After completion of the reaction, the solvent was distilled away and thereto n-hexane was added, which was successively washed with 5% aqueous solution of NaHCO$_3$, an aqueous solution of hydrochloric acid of pH 3 and saturated solution of salt, dried with magnesium sulfate and the solvent was distilled away to give 16.5 g of liquid. The obtained liquid was purified by silica-gel column chromatography (n-hexane:ethyl acetate=20:1) to give 10.6 g of the desired product. The obtained product was a mixture of the trans-form and the cis-form in a ratio of 5:1.

The obtained β-lactam had the following properties.
$[\alpha]_D^{25} = -6.0°$ (C=1, CCl$_4$)
$^1$HNMR (90MN$_z$, CDCl$_3$) δ(ppm):
Trans-form 0.03 (6H, s), 0.15 (6H, s), 0.60 (2H, d), 0.85 (9H, s), 0.90 (6H, d), 1.15 (3H, d), 1.80 (1H, m), 4.20 (1H, m), 4.95 (1H, dd) and 6.25 (1H, d)

REFERENCE EXAMPLE 6

[Preparation of (3R,4R)-4-acetoxy-3-[(R)-1-(dimethyl-1,1,2-trimethylpropylsilyloxy)ethyl]-azetidin-2-one]

There was dissolved 0.98 g of (3R,4R)-3-[1-dimethyl-1,1,2-trimethylpropylsilyloxy)ethyl]-4-trimethylsilyloxy-azetidin-2-one in 5 ml of methylene chloride and thereto 0.58 g of triethylamine and 0.66 g of dimethyl-1,1,2-trimethylpropylsilyl chloride were added and the mixture was stirred for 9 hours at room temperature. After completion of the reaction, the resultant mixture was washed with an aqueous solution of hydrochloric acid of pH 4 and the solvent was distilled away under reduced pressure to give 1.28 g of liquid crude product. There was added 1.27 g of the obtained liquid to 6 ml of methylene chloride, and thereto 0.95 g of dimethylaminopyridine and 1.59 g of acetic anhydride were further added and the mixture was reacted for 46 hours at $-15°$ C. After the solution was washed with 5% aqueous solution of NaHCO$_3$ and then water, the organic layer was separated and the solvent was distilled away under reduced pressure to give 1.27 g of liquid crude product. There was dissolved 1.19 g of the obtained liquid in 6 ml of methylene chloride, and to which 0.6 g of tetramethylammonium chloride and 0.3 g of potassium fluoride and 0.68 g of acetic acid were added and stirred for 2 hours at room temperature. After completion of reaction, the resultant mixture was washed with 5% aqueous solution of NaHCO$_3$ and then water, and the organic layer was separated and was condensed under reduced pressure to give 0.7 g of a solid crude product. Then, the obtained solid was recrystallized from hexane to give 0.35 g of the desired β-lactam as a solid.

The obtained β-lactam had the following properties.
mp: 80° to 81° C.
$[\alpha]_D^{25} = +41.6°$ (C=0.5, CHCl$_3$)
$^1$HNMR (90 MHz, CDCl$_3$) δ(ppm): 0.08 (6H, s), 0.65 (6H, s), 0.75 (6H, d), 1.15 (3H, d), 1.40 (1H, m), 2.08 (3H, s), 3.00 (1H, dd), 4.10 (1H, m), 5.71 (1H, d), 6.60 (NH)

REFERENCE EXAMPLE 7

[Preparation of (3R)-3-(dimethyl-1,1,2-trimethylpropylsilyloxy)-bute-1-nyl-trimethylsilyl ether]

There was added 3.8 g of (3R)-3-dimethyl-1,1,2-trimethylpropylsilyloxybutyl aldehyde to 20 ml of methylene chloride, 3.34 g of triethylamine and 4 ml of trimethylsilyl chloride were added to the above solution, and the mixture was refluxed for 24 hours. After completion of the reaction, the resultant mixture was washed with aqueous solution of hydrochloric acid of pH 4 and then water, and the solvent was distilled away to give 4.82 g of a crude product. The crude product was distilled under reduced pressure to give 3.5 g of the desired product (bp 98° C./2 mmHg). The obtained product was a mixture of the trans-form and the cis-form in a ratio of 10:1. The obtained β-lactam had the following properties.

$[\alpha]_D^{25} = -6.4°$ (c=1, CCl$_4$)
$^1$HNMR (90 MHz, CDCl$_3$) (Trans-form) δ(ppm): 0.01 (6H, s), 0.10 (9H, s), 0.75 (6H, s), 0.78 (6H, d), 1.10 (3H, d), 1.5 (1H, m), 4.15 (1H, m), 4.95 (1H, dd), 6.25 (1H, d)

What we claim is:

1. A β-lactam compound of the formula (I):

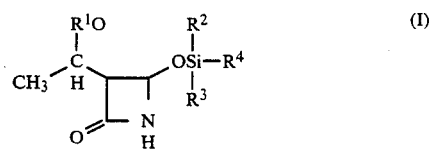

wherein R$^1$ is a trialkylsilyl group of the formula (II):

wherein each of R$^5$, R$^6$ and R$^7$ is independently a lower alkyl group, or R$^1$ is acetyl group, benzyloxycarbonyl group, o-nitrobenzyloxycarbonyl group, p-nitrobenzyloxycarbonyl group or t-butyl group, and each of R$^2$, R$^3$ and R$^4$ is independently a lower alkyl group having 1 to 4 carbon atoms, phenyl group or an aralkyl group.

2. The β-lactam compound of claim 1, wherein R$^1$ is a group of the formula (II):

wherein each of R$^5$, R$^6$ and R$^7$ is an alkyl group having 1 to 4 carbon atoms.

3. The β-lactam compound of claim 1, wherein R$^1$ is t-butyldimethylsilyl group.

* * * * *